United States Patent
Knobler

(10) Patent No.: US 9,693,993 B1
(45) Date of Patent: Jul. 4, 2017

(54) METHOD FOR TREATMENT OF MENOPAUSAL SYMPTOMS

(71) Applicant: Robert L. Knobler, Fort Washington, PA (US)

(72) Inventor: Robert L. Knobler, Fort Washington, PA (US)

(*) Notice: Subject to any disclaimer, the term of this patent is extended or adjusted under 35 U.S.C. 154(b) by 225 days.

(21) Appl. No.: 14/109,251

(22) Filed: Dec. 17, 2013

(51) Int. Cl.
*A61K 31/381* (2006.01)

(52) U.S. Cl.
CPC .................................. *A61K 31/381* (2013.01)

(58) Field of Classification Search
CPC ..................................................... A61K 31/381
See application file for complete search history.

(56) References Cited

U.S. PATENT DOCUMENTS

| 4,385,056 A * | 5/1983 | Loozen | C07C 62/34 514/254.08 |
| 2011/0178114 A1* | 7/2011 | Aung-din | A61K 9/0014 514/282 |

* cited by examiner

*Primary Examiner* — Sreeni Padmanabhan
*Assistant Examiner* — Jody Karol
(74) *Attorney, Agent, or Firm* — Andrew L. Salvatore, Esquire

(57) ABSTRACT

The subject invention describes a method of use of Rotigotine™ to alleviate and control menopausal symptoms in women, and in particular, hot flashes. The invention describes the use of Rotigotine as a dopamine agonist with affinity for the dopamine $D_2$, $D_3$, or $D_4$ receptors. The use of Rotigotine provides a useful new method for treatment of menopausal symptoms that are most disruptive to the functioning in activities of daily living.

3 Claims, No Drawings

METHOD FOR TREATMENT OF MENOPAUSAL SYMPTOMS

TECHNICAL FIELD

The subject invention relates to treatments and treatment methods of menopausal symptoms including hot flashes and sleep disturbance associated with menopause. Menopause and menopausal symptoms are controlled within the body by hormones which transmit information for the production or inhibition of various molecules which act to produce menopausal symptoms. The subject invention provides for a new method of treatment of menopausal symptoms which simulates the effect of naturally occurring neurotransmitters and thus aids in controlling menopausal symptoms.

BACKGROUND OF THE INVENTION

Menopause reflects the loss of function of the ovaries which affects all women at certain ages of their lifetimes. It typically begins naturally in middle age (late 40s through early 50s) over a period of time. However, menopause may occur more abruptly and earlier in certain medical conditions or when induced through surgical removal of the ovaries. The natural symptoms of menopause usually begin slowly, during a phase described as the menopausal transition or perimenopause, and can be devastating. These menopausal symptoms include irregular menses, hot flashes and night sweats, sleep disruption, atrophy of reproductive tissues, increased stress, tenderness of the breasts, vaginal dryness, mood changes, forgetfulness, and sometimes osteoporosis and heart disease.

One of the most prevalent symptoms is the typical "hot flash" which is a woman's perception of a sudden increase in body temperature followed by a sensation of feeling cold. The hot flash is the result of vascular changes which permit rapid increased blood flow through vessels. During a hot flash, the body temperature rises rapidly and then only slowly returns to its normal body temperature.

Various methods have been used to treat menopausal symptoms, and in particular, hot flashes. Hormonal Replacement Therapy (HRT) is a form of treatment which supplements naturally occurring hormones in the body. At normal levels, estrogen and progestin counter the effects of other hormones, such as luteinizing hormone (LH) and follicle stimulating hormone (FSH). During menopause, as estrogen and progestin levels are reduced, and levels of LH and FSH are found at high levels and menopausal symptoms become more apparent. http://en.wikipedia.org/wiki/Menopause (accessed Feb. 2, 2012), HRT treatment aims to supplement levels of estrogen and progestin to reduce levels of LH and FSH and thus reduce menopausal symptoms.

Increased levels of estrogen, though, create a risk of a number of other health risks including cancer, heart attack, and strokes. Decline in use of hormone therapy among postmenopausal women in the United Kingdom, *Menopause* 14 (3 Pt 1); 462-7; Differences in menopausal hormone therapy use among women in Germany between 1998 and 2003, *BMC Womens Health* 7: 19; Prescribing of hormone therapy for menopause, tibolone, and bisphosphonates in women in the UK between 1991 and 2005, *Eur. J. Clin. Pharmacol.* 63 (9): 843-9. Accordingly, HRT treatment may create potentially undesirable consequences far more devastating that the effects of menopausal symptoms, such as stimulating the growth of malignant cells.

Use of selective serotonin re-uptake inhibitors (SSRIs) and serotonin and norepinephrine re-uptake inhibitors (SNRIs) are other methods which have been used to treat menopausal symptoms. SSRIs and SNRIs have typically been used as antidepressants. SSRIs and SNRIs increase levels of serotonin by inhibiting its re-uptake into presynaptic cells. In theory, by increasing the levels of serotonin in the brain, the claimed benefits achieved as an anti-depressant, i.e. improving mood and promoting sleep, also serve to alleviate menopausal symptoms. However, the efficacy of SSRIs and SNRIs has been disputed. See Serotonin and Depression: A Disconnect between the Advertisements and the Scientific Literature, *PLoS Medicine* 2 (12): e392.

Selective Estrogen Receptor Modulators (SERMs) is another category of drugs which have been used to treat menopausal symptoms. These drugs act as agonists or antagonists to estrogen receptors throughout the body. However, it has been reported that most SERMs actually increase hot flashes, http://en.wikipedia.org/wiki/Menopause (accessed Feb. 2, 2012). See also Menopausal Symptoms, *Clin. Exp. Obstet. Gynecol.* 31 (2): 123-6]. Other drugs such as anti-seizure medications (i.e., gabapentin), and blood pressure medications (i.e., clonidine), have also been used to treat menopausal symptoms. http://en.wikipedia.org/wiki/Menopause (accessed Feb. 2, 2012). The mechanism of action of these agents is poorly understood, and the effectiveness of these treatments is disputed. Gabapentin for hot flashes in 420 women with breast cancer: a randomized double-blind placebo-controlled trial, *Lancet.* 366(9488); 818-24; Positive efficacy data from a phase 2 trial of gabapentin extended-release in the treatment of menopausal hot flashes, *Menopause*, 15(6); 1225; Nonhormonal Therapies for Menopausal Hot Flashes: Systematic Review and Meta-analysis, *JAMA*, 295(17):2057-71.

Natural regulation of menstrual cycles is controlled by complex interactions between various hormones and hormone producing glands within the body. The hypothalamus in the brain is a primary regulator of menstrual cycles. Hormones produced by the hypothalamus in the regulation of menstrual cycles include dopamine and prolactin. Dopamine inhibits the release of prolactin, while Thyrotropin Releasing Hormone (TRH) promotes the release of prolactin. Dopamine receptors in the body may be grouped into categories producing different effects depending on the type of receptor to which dopamine binds. Receptors of groups $D_2$, $D_3$, or $D_4$ produce effects contrary to those of group $D_1$ and $D_5$. D2 Dopamine receptor subtype mediates the inhibitory effect of dopamine on TRH-induced prolactin release from the bullfrog pituitary, *Gen. Comp. Endocrinology*, 168(2):287-92; Dopamine $D_1$ receptor analogues act centrally to stimulate prolactin secretion in ewes, *J. Endocrinology*, 137:457-64. Dopamine binding to receptors $D_2$, $D_3$, or $D_4$ in the hypothalamus will inhibit the production of prolactin, and also inhibit the pulsatile production of Gonadotropin Releasing Hormone (GnRH) in estrogen deficient females. Regulation of Gonadotropin-Releasing Hormone (GnRH)-Receptor Gene Expression in Tilapia: Effect of GnRH and Dopamine, *Biology of Reproduction*, 70:1545-51. It is the latter effect which in turn inhibits the production of LH and FSH in the pituitary gland in the estrogen deficient state of perimenopause and menopause. LH and FSH stimulate various functions in the reproductive and menstrual cycles. To the contrary, dopamine binding to the $D_1$ and $D_5$ receptors will stimulate the production of prolactin and will increase the production of GnRH thus leading to an increase in hot flashes. D2 Dopamine receptor subtype mediates the inhibitory effect of dopamine on TRH-induced prolactin release from the bullfrog pituitary, *Gen. Corp. Endocrinology*, 168(2):287-92.

LH and FSH are found at high levels during menopause. When levels of estrogen are higher, prior to menopause, estrogen provide a feedback loop which serves to limit the production of LH and FSH. However, during menopause, when levels of estrogen drop, levels of LH and FSH increase. Studies have shown that LH and FSH act as vasodilators which increase the flow of blood throughout the vessels. The increase in the flow of blood causes symptoms of hot flashes.

Drugs which activate a receptor to produce a pharmacological response are called agonists. These drugs may mimic the effect of the naturally occurring substance. An antagonist counteracts the pharmacological effect of a drug or a naturally occurring substance. U.S. Pat. No. 7,645,750 describes the use of certain drugs in the treatment of menopausal symptoms, in particular, hot flashes. In particular, the patent describes the use of risperidone, quetiapine, clozapine, olanzapine, aripiprazole, ziprasidone, zotepine, or 9-hydroxyrisperidone as serotonin type 2A ($5-HT_{2A}$) and dopamine type 2 ($D_2$) receptor antagonists. However, the efficacy of administering these drugs to treat menopausal symptoms has been disputed. The Safety of Verlipride, *Expert Opin. Drug Saf.* 5(5):695-71.

Given the risk of some of the current methods of treatment, and the failure of those methods to adequately treat and control menopausal symptoms such as hot flashes and sleep deprivation, there remains a need for improved means of addressing and treating these symptoms. The subject invention addresses these concerns and provides a new method of treatment of menopausal symptoms utilizing Rotigotine. As is discussed herein, the subject invention describes treatment with a dopamine agonist to provide relief of menopausal symptoms.

The subject invention describes a novel and new use of Rotigotine to alleviate and control menopausal symptoms in women, and in particular, hot flashes. The invention describes the use of Rotigotine as a dopamine agonist with affinity for the dopamine $D_2$, $D_3$, or $D_4$ receptors.

SUMMARY OF THE INVENTION

Rotigotine (Neupro) is a dopamine agonist. Typically, Rotigotine has been used in the treatment of Parkinson's disease and Willis-Ekbom Disease. Nightwalkers: Willis-Ekbom Foundation; Winter 2013 issue. Rotigotine has also been shown to have antidepresent effects. Bertaina-Anglade V, La Rochelle C D, Scheller D K (October 2006). Antidepressant properties of Rotigotine in experimental models of depression, *European Journal of Pharmacology* 548 (1-3): 106-14.

The chemical formula of Rotigotine is as follows: (S)-6-[propyl(2-thiophen-2-ylethyl)amino]-5,6,7,8-tetrahydronaphthalen-1-ol, and the chemical model is depicted as follows:

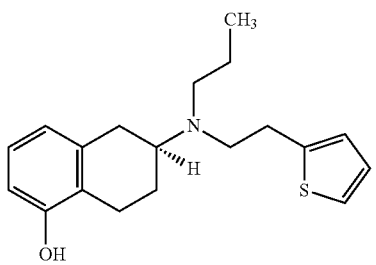 [SMILES: CCCN(CCc1cccs1)[C@H]1CCc2c(O)cccc2C1]

in vitro experimental data has shown Rotigotine to have the following binding affinities to dopamine receptors.

$D_1$ receptor ($K_i$=83 nM)
$D_2$ receptor ($K_i$=13.5 nM)
$D_3$ receptor ($K_i$=0.71 nM)
$D_{4.2}$ receptor ($K_i$=3.9 nM)
$D_{4.4}$ receptor ($K_i$=15 nM)
$D_{4.7}$ receptor ($K_i$=5.9 nM)
$D_5$ receptor ($K_i$=5.4 nM)

Scheller D, Ulmer C, Berkels R, Gwarek M, Lübbert H (January 2009). "The in vitro receptor profile of rotigotine: a new agent for the treatment of Parkinson's disease," *Naunyn-Schmiedeberg's Archives of Pharmacology* 379 (1): 73-86. The binding affinity to a particular receptor decreases with increases $K_i$ values, i.e. it takes a greater concentration of Rotigotine to saturate the receptor. (Notably, although Rotigotine has a relatively lower binding affinity to the $D_5$ receptor, it is theorized that $D_5$ is not as significant in menopausal response and so does not affect hot flashes. It is alternately theorized that the net effect of binding to $D_2$, $D_3$, and $D_4$ outweighs any adverse effects through binding with $D_5$.)

Rotigotine also has affinity for adrenergic and other receptors. However, it has particular affinity to $D_2$ like receptors and behaves mostly as a selective $D_2$-like ($D_2$, $D_3$, $D_4$) and $D_5$ receptor agonist. Scheller D, Ullmer C, Berkels R, Gwarek M, Lübbert H (January 2009). The in vitro receptor profile of Rotigotine: a new agent for the treatment of Parkinson's disease, *Naunyn-Schmiedeberg's Archives of Pharmacology* 379 (1): 73-86. Rotigotine has shown agonistic activity on all dopamine receptors "with a clear (about 20-fold) preference for the D3 over the D2 and (about 100-fold) over the D1 receptor." Jenner, P. (2005). A novel dopamine agonist for the transdermal treatment of Parkinson's disease, *Neurology*, 65 (Suppl 1):53-5. Rotigotine has a high affinity for the $D_3$ dopamine receptor. Cawello, W. (2009). Absorption, Disposition, Metabolic Fate, and Elimination of the Dopamine Agonist Rotigotine in Man: Administration by Intravenous Infusion or Transdermal Delivery, *The American Society For Pharmacology And Experimental Therapeutics* 37:2055-2060.

Although, Rotigotine has been used for treatment of various medical conditions as noted above, it has not previously been studied or used in the treatment of menopausal symptoms, except by the inventor as noted herein. Binding of Rotigotine to $D_2$, $D_3$, or $D_4$ in the hypothalamus will act as a dopamine agonist to inhibit the production of prolactin and GnRH which inhibits production of LH and FSH. Accordingly, treatment with Rotigotine will serve to reduce the incidence of hot flashes and other symptoms associated with menopause.

It is believed that Rotigotine reduces production of GnRH which in turn reduces production of LH and FSH. The use of Rotigotine as a menopausal symptom treatment overcomes the limitations of the prior art as it does not pose some of the significant health effects and side effects associated with HRT therapy and use of anti-depressant medication such as SSRIs.

DETAILED DESCRIPTION OF INVENTION

Hot flashes of menopause are vasomotor events characterized by sudden bursts of intense warmth in the chest, which may ascend to the neck and face. This feature is often accompanied by profuse sweating, skin blotching and possibly even palpitations and anxiety. Estimates suggest a prevalence of 75% in postmenopausal women, with an onset of one to two years prior to menopause and a duration of six months to five years.

Hot flashes can be particularly disruptive at night, initially causing drenching sweats followed by a sensation of cold, interrupting sleep separately from the sleep disturbance of menopause.

During the day, hot flashes can impede an affected individual's ability to function effectively with negative consequences on job performance, quality of life and self-esteem. Although generally appreciated as a condition affecting women, hot flashes can also affect as many as 75% of men following hormonal ablation therapy in the treatment of prostate cancer.

Although the precise mechanism causing hot flashes remains unknown at present, their onset occurring in concert with the withdrawal of end organ hormones, such as estrogen in the female and testosterone in the male, suggests a causal relationship. This is supported by the responsiveness of resolution of symptoms by women treated with Hormone Replacement Therapy (HRT).

Unfortunately, efforts to treat hot flashes in women with HRT, although generally successful in 80-90% of women, are now also recognized to place women with a personal or family history of breast cancer, ovarian cancer, uterine cancer, venous thromboembolism, cardiovascular disease, stroke or a positive smoking history, at increased risk.

Women who undergo rapid end organ hormonal withdrawal due to medical/surgical menopause, such those undergoing total abdominal hysterectomy, or survivors of either breast cancer or ovarian cancer subjected to hormonal blocking therapies (aromatase inhibitors to block hormone synthesis or tamoxifen to block hormone receptors), are inherently more sensitive to the development of hot flashes.

Withdrawal of end organ steroid hormones are accompanied by a predictable rise in pituitary gonadotrophins. In women there is a measurable rise in luteinizing hormone (LH) and follicle stimulating hormone (FSH). Factors contributing to this increase are not only the decline in end organ steroid hormones, but the impact of changes in other relevant molecules such as inhibin.

Efforts to control hot flashes have initially focused primarily on HRT, with the goal of restoring estrogen to suppress the hypothalamic-pituitary-gonadal axis through which the hot flashes are believed to be mediated. Due to the side effects of HRT, alternatives have been sought over the course of the past decade. Although natural supplements have been advocated, these tend to be rich in phytoestrogens, so they are predisposed to the same concerns which have dissuaded the regular use of HRT.

In contrast, with the availability of later generation dopaminergic agonists such as Rotigotine, there is now the opportunity to intervene in the putative hormonal feedback loop without the use of hormones. Just as dopamine can interfere with the release of the pituitary hormone prolactin, a dopamine agonist may also impede the release of the hypothalamic gonadotrophic hormone, GnRH. Rotigotine is a dopamine agonist with particular affinity to $D_2$ like receptors and behaves mostly as a selective $D_2$-like ($D_2$, $D_3$, $D_4$) and $D_5$ receptor agonist. Scheller D, Ullmer C, Berkels R, Gwarek M, Lübbert H (January 2009). The in vitro receptor profile of rotigotine: a new agent for the treatment of Parkinson's disease, *Naunyn-Schmiedeberg's Archives of Pharmacology* 379 (1): 73-86. It is believed that Rotigotine impacts the biofeedback path to control GnRH, and reduces hot flashes. The mechanism of action is postulated to be mediated through the down-regulatory role of dopamine on prolactin and gonadotropin releasing hormone, which would influence the pulsatile unbridled release of LH and FSH of menopause. Rotigotine is a well-tolerated medication, with an excellent safety profile.

The invention contemplates that various forms may be used to administer Rotigotine. In the treatment of Parkinson's disease, Rotigotine has been administered through use of a transdermal patch. A similar means of administration for treatment of menopausal symptoms may be used. However, the invention contemplates that Rotigotine may be administered in other forms such as in a pill form or in a liquid format, either orally or intravenously. Another method of drug administration may be inhalation of the compound. The invention also contemplates that Rotigotine may be administered by other known means of administering the drug.

Additionally, the invention contemplates that other chemical compounds having the properties of Rotigotine and producing the same effects may also be used in place of Rotigotine. For instance, compounds acting as a dopamine agonist and binding at the $D_2$, $D_3$, or $D_4$ dopamine receptors may also be used for relief of menopausal symptoms, and in particular, hot flashes.

Rotigotine has never previously been used for the treatment of menopausal symptoms. However, Rotigotine's affinity to the $D_2$, $D_3$, or $D_4$ dopamine receptors triggers the same series of biochemical reactions which inhibit the production of prolaction and GnRH and thus inhibit production of LH and FSH. Accordingly, use of Rotigotine for treatment of menopausal symptoms represents a new use of the drug not previously realized.

Clinical Studies

The efficacy of Rotigotine in treating incapacitating menopausal symptoms of hot flashes (vasomotor symptoms) has been demonstrated through empirical studies of the treatment of women with these symptoms. The patients were treated by escalating the dose of Rotigotine, starting with the lowest available dose of 1 mg per day, and escalating to 2 mg per day, with the potential of reaching a maximum dose of 4 mg per day if necessary. This was done to test the hypothesis of relieving vasomotor symptoms of hot flashes through influencing a dopaminergically regulated pathway within the central nervous system. The dopaminergic agonist Rotigotine was escalated from the initial dose of 1 mg per day to a final dose of 2 mg per day without side effects and with the dramatic shutdown of previously intolerable vasomotor symptoms of menopause of hot flashes.

Case Study

BM, a 54 year old woman, began experiencing vasomotor symptoms of hot flashes as the earliest feature of menopause. She was not a candidate for Hormone Replacement Therapy (HRT) because of an underlying clotting disorder, with a prior history of both deep vein thrombosis and pulmonary embolism, and she was being treated with medication (Lovenox) to prevent recurrence of those disorders.

Despite multiple efforts to control her vasomotor symptoms of menopause with non-hormonal therapies such as gabapentin, venlafaxine and clonidine, these hot flashes continued throughout the day. The other medical alternatives reported to have success in reducing hot flash frequency and severity by as much as 50% were evaluated by titrating to their recommended doses, and maintaining those doses for at least a two week trial. These included gabapentin at a dose of up to 1800 mg per day, venflaxamine at a dose of up to 300 mg per day and clonidine at a dose up to 0.4 mg per day, each medication evaluated independently of the others.

However, these were not satisfactory in reducing hot flashes by more than 25% in this individual.

There either was no clinical effect or intolerable side effects associated with those agents, and a better alternative had to be found. In addition, she was experiencing problems diagnosed as restless legs syndrome, consisting of an irresistible urge to move her legs to stop an uncomfortable irritating sensation that responded to movement. Her symptoms of motor restlessness were worsened by immobilization and relieved by movement, and they felt worst at the end of the day. The restless legs syndrome provided a rationale for utilizing Rotigotine, an FDA-approved dopamine agonist medication as an approved symptomatic treatment for that diagnosis. Although the use of the 1 mg patch provided dramatic reduction of the restless legs syndrome and the frequency and severity of the vasomotor symptoms of menopause (hot flashes), she did not have complete relief until the daily dose was raised to 2 mg per day.

Prior to treatment, each hot flash would typically last 30-90 seconds and was accompanied by an intense sensation of heat. The hot flash would then rapidly subside and she experienced a sense of feeling chilled, reflecting the normal physiologic function of evaporation of her perspiration. A period of 10 to 90 minutes would elapse before the next hot flash would occur. These episodes occurred both during the daytime and throughout the night. It was common for there to be between 20 to 30, and as many as 40 hot flashes over the course of a day at their peak in frequency, although not all would be of the same intensity.

After Rotigotine treatment was initiated at 1 mg per day, the frequency of hot flashes dropped to three or four flashes per day, with intervals of several hours between the flashes. The severity was reduced, with less intensity of the sweating, and the duration of the hot flash was reduced to no longer than 30 seconds. These effects were readily noticeable. Safety monitoring included making certain there were no issues with nausea, liver function, low blood pressure or unusual dreams as her treatment was continued. There was no "hangover" effect or sleepiness throughout the day. Rotigotine titration was initiated with a 1 mg at bedtime, and if tolerated, by escalating the dose by 1 mg every second week, with a maximal dose of 4 mg, until there was elimination of both the frequency and severity of hot flashes. The maximal dose available in clinical practice is 8 mg, so the dose range for control of the vasomotor symptoms of menopause are well below that dose. Higher Rotigotine doses were not needed to accomplish clinical suppression of the vasomotor symptoms of menopause (hot flashes) in this woman, but were not tested either due to a greater likelihood of potential side effects such as nausea, hallucinations or jitteriness.

The Rotigotine patch represented a new, non-hormonal method of treating vasomotor symptoms of menopause (hot flashes) effectively and with minimal side effects. This response was highly significant and a dramatically notable improvement compared to other approved options that are available. Rotigotine was shown to reduce hot flashes as a dopamine agonist with maximal effectiveness on the $D_2$, $D_3$ and $D_4$ receptors, totally eliminating the most severe form of hot flashes, with the most intense vasomotor symptoms. It completely stopped the frequency and intensity of these symptoms. When the dose of Rotigotine was temporarily withdrawn, due to issues of availability, the symptoms returned. When the Rotigotine was re-administered at 2 mg per day, the vasomotor symptoms of menopause (hot flashes) once again completely disappeared.

The most incapacitating symptom of menopause is due to vasomotor symptoms (hot flashes). Although there have been many attempts to address this symptom, hormonal and non-hormonal treatment methods provided thus far do not adequately resolve this symptom, and many have also created additional health risks.

With Rotigotine, the mechanism of action in reducing vasomotor symptoms of hot flashes is directed at regulating GnRH, and controlling the unsuppressed LH pulses characteristic of menopause, through the action on $D_2$ and $D_3$ receptors within the hypothalamus. Prior ineffective dopamine agonists which have been used for this purpose have had opposite actions on these molecules because they worked primarily upon the $D_1$ and $D_5$ receptors. The overall responses of the $D_1$ and $D_5$ receptors vs. the $D_2$, $D_3$ and $D_4$ receptors are diametrically opposed.

The subject invention describes a novel and new use of the dopamine agonist Rotigotine to alleviate and control of vasomotor symptoms of menopause in women (hot flashes). As a dopamine agonist, Rotigotine is believed to bind most strongly to the $D_2$, $D_3$, or $D_4$ receptors, particularly at the $D_3$ site. This affinity inhibits production of GnRH which reduces production of LH and FSH in the pituitary. LH and FSH are vasodilators, and lower levels of LH and FSH result in reduced incidence of hot flashes.

Clinical studies have shown that treatment with Rotigotine significantly eliminated vasomotor symptoms of menopause (hot flashes). The use of Rotigotine as a symptomatic treatment of menopause overcomes the limitations of the prior art as it does not pose the significant health effects and side effects associated with these other treatment methods. Further, empirical clinical studies have shown the use of Rotigotine to have a much greater efficacy than either traditional hormonal treatments of vasomotor symptoms of menopause, or other forms of non-hormonal treatment.

The invention has been disclosed in terms of preferred embodiments which fulfill all of the objects of the present invention and overcome the limitations of the prior art. Various changes, modifications, and alterations from the teachings of the present invention may be contemplated by those skilled in the art without departing from the intended spirit and scope thereof. It is intended that the present invention only be limited by the terms of the appended claims.

What is claimed is:

1. A method of treatment of menopausal symptoms comprising the steps of: administering an effective amount of a chemical compound to a person experiencing menopausal symptoms, the compound being a dopamine agonist capable of binding to $D_2$, $D_3$, or $D_4$ dopamine receptors and the compound having the chemical formula (S)-6-[propyl(2-thiophen-2-ylethyl)amino]-5,6,7,8-tetrahydronaphthalen-1-ol, and evaluating the effects of administration of the compound.

2. A method of treatment of menopausal symptoms as set forth in claim 1 wherein the effective amount of the chemical compound is administered in a range from 1 mg to 4 mg per day.

3. A method of treatment of menopausal symptoms as set forth in claim 1 wherein the method of administration of the chemical compound is selected from the group consisting of administration of the compound in a pill, administration of the compound orally in a liquid form, administration of the compound intravenously in a liquid form, administration of the compound using a transdermal patch, and administration of the compound by inhalation.

* * * * *